United States Patent

Forman et al.

[11] Patent Number: 5,948,439
[45] Date of Patent: Sep. 7, 1999

[54] EFFERVESCENT GRANULES

[75] Inventors: Yochanan Forman, Kibbutz Maabarot; Orna Levin, Kfar-Neter; Doron Friedman, Karme-Yosef; Michael Friedman, Jerusalem, all of Israel

[73] Assignee: Farmo-Nat Ltd., Ashkelon, Israel

[21] Appl. No.: 08/962,118

[22] Filed: Oct. 31, 1997

[51] Int. Cl.⁶ ................ A61K 9/16; A61K 9/48
[52] U.S. Cl. ................................................ 424/466
[58] Field of Search ................ 424/466, 195.1, 424/489

[56] References Cited

U.S. PATENT DOCUMENTS 3,888,976  6/1975  Mlkvy et al. .................... 424/44

Primary Examiner—Thurman K. Page
Assistant Examiner—James M. Spear
Attorney, Agent, or Firm—Mark M. Friedman

[57] ABSTRACT

An effervescent granule for the release and efficient dispersion of a herbal preparation in water. Also provided is a method of making the phytomedicated granule and a method of using the granule. The granule of the present invention is particularly efficient for the dispersion of a herbal preparation which includes an essential oil, although herbal preparations including an herbal extract can also be used.

17 Claims, No Drawings

EFFERVESCENT GRANULES

FIELD AND BACKGROUND OF THE INVENTION

The present invention relates to effervescent granules containing an herbal preparation. In particular, the present invention relates to effervescent granules which can conveniently and rapidly disperse beneficial herbal extracts, essential oils, or both, into bathing water for topical administration or into steam for inhalation.

Herbal medicines in the form of extracts or essential oils are very benefitial in forms such as medicinal baths or rinses, or in a form which permits inhalation of medicinal vapors. Hereinafter, the term "herbal medication" refers to a medication derived from botanical materials or a biologically active extract of these materials. However, currently available formulations of these herbal medicines require elaborate preparation before use, which makes these formulations inconvenient to use and hampers patient compliance. Also, from a technical perspective, one form of such medications, essential oil, does not dissolve and disperse well in water.

There is thus a widely recognized need for, and it would be highly advantageous to have, a formulation which enhances the dispersion and dissolution of herbal medicines in water, which enables all forms of these herbal medicines to dissolve easily and efficiently in water, and which enables these medicines to be used in bathing water or to be inhaled in the form of steam.

SUMMARY OF THE INVENTION

According to the present invention, there is provided an effervescent granule, including: (a) a pharmaceutically effective amount of a herbal medication; (b) an acid; and (c) a base capable of releasing carbon dioxide upon reaction with the acid when contacted with water. Preferably, the acid is selected from the group consisting of tartaric acid and citric acid. Alternatively and preferably, the acid is a mixture of tartaric acid and citric acid. More preferably, the tartaric acid and the citric acid are present in a ratio of about 2:1 by weight. Also preferably, the base is selected from the group consisting of sodium bicarbonate, sodium carbonate and potassium bicarbonate. More preferably, the base is sodium bicarbonate. Most preferably, the acid is a mixture of citric acid and tartaric acid, and the sodium bicarbonate, the citric acid and the tartaric acid are present in a ratio of about 3.44:1:2 by weight.

According to another embodiment of the present invention, there is provided a method of releasing and evenly dispersing a medication in water, including the steps of: (a) providing an effervescent granule, the granule including: (i) a pharmaceutically effective amount of a herbal medication as the medication; (ii) an acid; and (iii) a base capable of releasing carbon dioxide upon reaction with the acid; and (b) placing the granule in water, such that the medication is released upon reaction of the acid and the base.

Hereinafter, the term "herbal medication" can include one or more herbal extracts, one or more essential oils, or a combination of both.

Herbal extracts are extracts of plant materials. Preferably, herbal extracts are a tincture of botanical materials, which are prepared by contacting botanical material with a solvent [*British Herbal Pharmacopeia*, Peter R. Bradley, ed., British Herbal Medicine Association, 1983; and *British Herbal Compendium*, Peter R. Bradley, ed., British Herbal Medicine Association, 1992]. The solvent can be aqueous or organic, or a combination thereof. Acceptable organic solvents include, but are not limited to, glycerin, propylene glycol or alcohol, or a combination thereof. The most preferred solvents are hydroalcoholic solvents as defined in *British Herbal Pharmacopeia and Compendium*. The botanical material can include, but is not limited to, one or more of the following species: Plantago (*Plantago major*), Hypericum (*Hypericaceae perforatus*), Echinacea (Coneflower) (Echinaceae species such as *Echinaceae angustifoliae* radix and *Echinaceae purpurea*), Baptisia, Calendula, Myrrh, Phytolaca, Salvia, Catechu black, Krameria, Tsuga, Rosmarinus, Styrax, Crataegus, Glycerrhiza (*Glycerrhiza glabra*), Angelica, Krameria, Matricaria, Mallow and Sage. Propolis is the resinous substance found in beehives. Although strictly speaking Propolis is not a botanical material, extracts of this material are prepared in a substantially similar manner as extracts of the plant materials and are hereinafter included in the term "herbal extract".

Although essential oils can also be described as a "herbal extract", generally such oils are considered to be a separate entity from the tinctures described above. As used herein, the term "herbal extract" refers to a tincture as described previously. An essential oil is a volatile mixture of esters, aldehydes, alcohols, ketones and terpenes, which can be prepared from botanical materials or plant cell biomass from cell culture. Examples of essential oils include, but are not limited to, oil of cinnamon, prepared from the dried bark of the roots of *Cinnamomum zeyloriaceae*, cajeput oil, eucalyptus oil, prepared from the fresh leaves and branches of various species of Eucalyptus, such as *E. globulus*; fennel oil, prepared from dried ripe fruit of *Foeniculum vulgare*; geranium oil, prepared from the aerial parts of Pelargonium species; girofle oil, lavander oil, prepared from fresh flowering tops of Lavandula species such as *Lavandula officinalis*; lemon oil, obtained from the fresh peel of *Citrus limon*; spearmint oil, prepared from the overground parts of fresh flowering Mentha species, such as *M. spicata*; myrte oil, origano oil, pine oil, rosemary oil, prepared from tops or leafy twigs of *Rosmarinus officinalis*; sarriette oil, thyme oil, prepared from the leaves and flowering tops of *Thymus vulgaris*; juniper oil, melissa oil, borneal oil, matricaria oil, cupressus oil and tea-tree oil, obtained from the leaves of *Melaleuca olternifolia*.

DESCRIPTION OF THE PREFERRED EMBODIMENTS

The present invention is of effervescent granules for the release and efficient dispersion of herbal medicines into bathing water for topical administration, or into steam for inhalation. These effervescent granules enable both herbal extracts and essential oils to be evenly and efficiently dispersed in water. This is particularly beneficial for essential oils which, as their names suggests, are oils and therefore do not disperse well in water alone. Furthermore, the granules of the present invention are specifically designed to be used with herbal medications.

Effervescent salts have classically been used to disperse medicines in water for oral administration. Effervescent salts are granules or coarse powders containing a medicinal agent in a dry mixture, usually composed of sodium bicarbonate, citric acid and tartaric acid. When the salts are added to water, the acids and the base react to liberate carbon dioxide gas, thereby causing "effervescence". The resultant carbonated solution masks the usually saline or otherwise undesirable taste of the medicinal agent present. By using granules or coarse particles, rather than fine powder, the contact area of the substances is decreased, and the otherwise violent reaction and rapid uncontrollable effervescence is eliminated.

The properties of these salts are also useful for introduction and dispersion of herbal preparations in water for bathing. Hereinafter, the term "bathing" includes topically contacting at least a portion of the body with an aqueous solution. The solution could be water alone, or water with one or more additives. For the present invention, generally the skin will be contacted with water containing a herbal preparation. The herbal preparation could include one or more herbal extracts, one or more essential oils, or both. The effervescent salts of the present invention are particularly effective for the dispersion of essential oils in water, thereby overcoming the hydrophobicity of these oils. Thus, the salts enable herbal preparations containing one or more essential oils to be easily administered as a topical formulation in bathing water.

Formulation of Effervescent Granules

The choice of ingredients for effervescent granules depends both upon the requirements of the manufacturing process and the necessity of making a preparation which dissolves readily in water. The two required ingredients are at least one acid and at least one base. The base must release carbon dioxide upon reaction with the acid. Examples of such acids include, but are not limited to, tartaric acid and citric acid. Preferably, the acid is a combination of both tartaric acid and citric acid. Examples of bases include, but are not limited to, sodium carbonate, potassium bicarbonate and sodium bicarbonate. Preferably, the base is sodium bicarbonate.

Effervescent granules are usually prepared from a combination of citric and tartaric acid rather then from a single acid because the use of either acid alone causes difficulties. When tartaric acid is the sole acid, the resulting granules readily crumble. Citric acid alone results in a sticky mixture which is difficult to granulate during the manufacturing process, as described below.

Effervescent salts preferably include the following ingredients, which actually produce the effervescence: sodium bicarbonate, citric acid and tartaric acid. When added to water the acids and base react to liberate carbon dioxide, resulting in effervescence. It should be noted that any acid-base combination which results in the liberation of carbon dioxide could be used in place of the combination of sodium bicarbonate and citric and tartaric acids, as long as the ingredients were suitable for pharmaceutical use.

The reactions between citric acid and sodium bicarbonate (1) and tartaric acid and sodium bicarbonate (2), which results in the liberation of carbon dioxide gas, may be shown as follows:

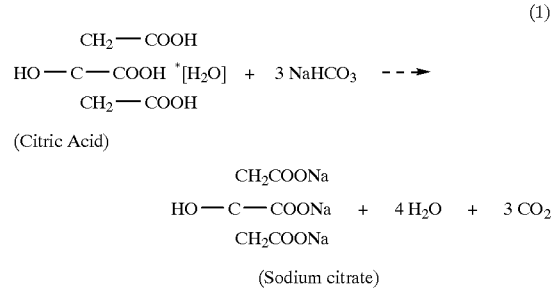

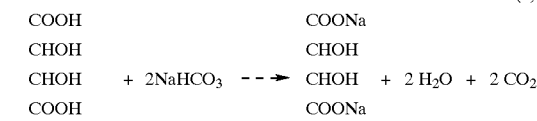

(Tartaric Acid) (Sodium Tartarate)

Net reaction:

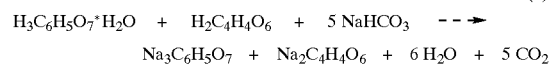

It should be noted that it is requires 3 molecules of $NaHCO_3$ (sodium bicarbonate) to neutralize 1 molecule of citric acid (1) and 2 molecules of $NaHCO_3$ to neutralize 1 molecule of tartaric acid (2). The proportion of acids may be varied, so long as the total acidity is maintained and the bicarbonate completely neutralized. Usually it is desired that ratio of citric acid to tartaric acid equal 1:2, so that the desired ratio of ingredients can be calculated as follows Citric Acid:Tartaric Acid:Sodium Bicarbonate=1:2:3.44 (by weight).

Of course, this ratio could be varied within a fairly wide range of values as defined in the prior art and still provide a reasonably efficient release of carbon dioxide. For example, ratios of 1:0:3 or 0:1:2 would also be effective. The selection of a specific ratio of ingredients could easily be determined by one of ordinary skill in the art, according to the desired properties of the final formulation.

Methods of Preparing Effervescent Granules

The method of preparation of the granules of the present invention is as follows. There are three basic methods: wet and dry granulation, and fusion. The fusion method is the preferred method of preparation for effervescent granules, although the other two methods can also be used. Indeed, the fusion method is used for the preparation of most commercial effervescent powders. It should be noted that although these methods are intended for the preparation of granules, the formulations of effervescent salts of the present invention could also be prepared as tablets, according to well known prior art technology for tablet preparation. Such a tablet could also be used for dissolution in bathing water or in boiling water for steam inhalation.

Wet Granulation

This is the oldest method of granule preparation, although it suffers from problems of reproducibility. The individual steps in the wet granulation process of tablet preparation include milling and sieving of the ingredients; dry powder mixing; wet massing; granulation; and final grinding.

Wet massing of the most important steps in the wet granulation process. In this step, the granulation agent is added to the powder mixture. At the end of wet massing, the damp powder will pack to the consistency of a dry snowball, and crumble into fragments, not powder, under finger pressure. The granulation agent may be water added to a solvent, such as alcohol, which is employed as the moistening agent.

In the granulation step, the granules themselves are formed by forcing the moistened powder through a screen in an oscillation granulator or in a hammer mill. The resulting granulated material is dried on trays in a hot air circulation oven or preferably in a fluid bed drier.

Particles may agglomerate and lump during drying, particularly in an oven. Therefore a sizing or dry screening operation is usually required after drying. An oscillation granulator is often used for this sizing step. The screen used for sizing should have slightly larger openings then that used to prepare the original granules if excessive powder is not to be formed and granulation lost during sizing. If, for example, 20-mesh screen is used for granulation, a 16-mesh screen would be a good selection for sizing.

Dry Granulation

Typically, the process involves compressing a powder mixture into a rough tablet or "slug" on a heavy-duty rotary tablet press. The slugs are then broken up into granular particles by a grinding operation, usually by passage through an oscillation granulator. The individual steps include mixing of the powders; compressing (slugging); and grinding (slug reduction or granulation. No wet binder or moisture is involved in any of the steps.

Fusion Method

The most preferred method for preparing the granules of the present invention is the fusion method. In this method, the compressing (slugging) step of the dry granulation process is eliminated. Instead, the powders are heated in an oven or other suitable source of heat. The particular advantage of this process is that it uses the water molecule complexed with each molecule of citric acid as the granulation, or binding agent. Just before mixing the powders, the citric acid crystals are powdered and then mixed with the other powders (previously passed through a number 60 sieve) to ensure uniformity of the mixture. The sieves and the mixing equipment should be made of stainless steel or other material resistant to the effects of the acids. The mixing of the powders is performed as rapidly as is practical, preferably in an environment of low humidity to avoid the absorption of moisture from the air by the chemicals and a premature chemical reaction. After mixing the powder is placed on a plate or glass or a suitable dish in an oven previously heated to between 93° and 104° C. During the heating process the powder must be turned over.

The heat causes the release of the water of crystallization from the citric acid. The released water then dissolves a portion of the powder mixture and causes the chemical reaction to start, with the consequent release of some carbon dioxide. This causes the softened mass of powder to become somewhat spongy, and when of the proper consistency, similar to bread dough, the mass is removed from the oven and rubbed through an acid resistant sieve to produce granules of the desired size. A No. 4 sieve may be used to produce large granules, while a No. 8 sieve can be used to prepare small granules. When all of the mass has passed through the sieve, the granules are immediately dried at a temperature not exceeding 54° C. and immediately transferred to containers which are then tightly sealed.

Specific Examples

A number of examples of formulations of effervescent granules according to the present invention are given below for purposes of illustration only and are not intended to be limiting. Ingredients are given as a percentage, weight per weight, of the final product.

EXAMPLE 1

In this example, as in all further examples given below, the acid and base combination is citric acid, tartaric acid and sodium bicarbonate. The leaves and flowers of Rosmarini and Eucalypti plants, and the fruits of Juniperi plants were used to prepare the dry herbal extracts. Oleum pini, or pine oil, and Thyme oil are the essential oils.

| Ingredients | % w/w (weight per weight) |
| --- | --- |
| Citric Acid | 12.0 |
| Tartaric Acid | 24.0 |
| Sodium Bicarbonate | 39.0 |
| Rosmarini | 4.0 |
| Eucalypti | 8.0 |
| Juniperi | 8.0 |
| Oleum pini | 2.5 |
| Thyme oil | 2.5 |

EXAMPLE 2

In this example, extracts prepared from *Phytolacca decand., Calendula offic., Echinacea purpurea* and Propolis extract are the dry herbal extracts. Tea Tree oil and Thyme oil are the essential oils.

| Ingredients | % w/w |
| --- | --- |
| Citric Acid | 14.0 |
| Tartaric Acid | 28.1 |
| Sodium Bicarbonate | 47.9 |
| *Phytolacca decand.* | 4.0 |
| *Calendula offic.* | 2.0 |
| *Ectinacea purpurea* | 1.0 |
| Propolis extract | 1.0 |
| Tea Tree oil | 1.0 |
| Thyme oil | 1.0 |

EXAMPLE 3

In this example, extracts prepared from Harpagophytum, Hammamelis and Arnica plants are the dry herbal extracts. Lavendula oil and Rosmarinus oil are the essential oils.

| Ingredients | % w/w |
| --- | --- |
| Citric Acid | 14.0 |
| Tartaric Acid | 28.1 |
| Sodium Bicarbonate | 47.9 |
| Harpagophytum | 4.0 |
| Hammamelis | 2.0 |
| Arnica | 2.0 |
| Lavendula oil | 1.0 |
| Rosmarinus oil | 1.0 |

EXAMPLE 4

In this example, extracts prepared from Calendula, Stelloria and Hammamelis plants are the dry herbal extracts. Chamomile oil and Juniperus oil are the essential oils.

| Ingredients | % w/w |
| --- | --- |
| Citric Acid | 13.0 |
| Tartaric Acid | 26.0 |
| Sodium Bicarbonate | 48.0 |
| Calendula | 3.0 |
| Stelloria | 3.0 |
| Hammamelis | 3.0 |
| Chamomile oil | 2.0 |
| Juniperus oil | 2.0 |

EXAMPLE 5

In this example, extracts prepared from Willow (Salix Albe) bark, *Hammamelis virgin, Calendula effic.* and *Har-*

*pegophytum procume* are the dry herbal extracts. Menthol, Lavender oil and Geranium oil are the essential oils.

| Ingredients | % w/w |
| --- | --- |
| Citric Acid | 12.0 |
| Tartaric Acid | 24.0 |
| Sodium Bicarbonate | 41.1 |
| Willow (*Salix Albe*) bark | 6.0 |
| Hammamelis virgin | 5.0 |
| *Calendula effic* | 5.0 |
| *Harpegophytum procume* | 3.9 |
| Menthol | 1.0 |
| Lavender oil | 1.0 |
| Geranium oil | 1.0 |

EXAMPLE 6

In this example, extracts prepared from Arcticum Lappa, *Stellaria media, Calendula offic.*, Hamamelis and *Symphytum offic.* plants are the dry herbal extracts. Thyme oil and *Ornanum majorana* oil are the essential oils.

| Ingredients | % w/w |
| --- | --- |
| Citric Acid | 14.0 |
| Tartaric Acid | 28.1 |
| Sodium Bicarbonate | 47.9 |
| *Arcticum Lappa* | 2.0 |
| *Stellaria media* | 1.0 |
| *Calendula offic.* | 1.0 |
| Hamamelis | 1.0 |
| *Symphytum offic.* | 1.0 |
| Thyme oil | 2.0 |
| Ornanum marjorana oil | 2.0 |

EXAMPLE 7

In this example, there are no dry herbal extracts. Instead, a mixture of essential oils is used: Lavandula, Rosmarinus, Eucalyptus, Pine, Thymus, Citrus Limonum and Menthol. This represents a potentially difficult combination for dissolution into water, since such a large portion of the ingredients are oils. However, effervescent granules of the present invention are able to overcome this difficulty and promote even and efficient dispersion of such oils, thereby illustrating one advantage of these granules.

| Ingredients | % w/w |
| --- | --- |
| Citric Acid | 14.0 |
| Tartaric Acid | 28.1 |
| Sodium Bicarbonate | 47.9 |
| Lavandula | 1.0 |
| Rosmarinus | 1.0 |
| Eucalyptus | 2.0 |
| Pinus | 2.0 |
| Thymus | 2.0 |
| Citrus Limonum | 1.0 |
| Menthol | 1.0 |

EXAMPLE 8

In this example, extracts prepared from Rotunculus, Symphytum and Calendula plants are the dry herbal extracts. Cupressus oil is the essential oil.

| Ingredients | % w/w |
| --- | --- |
| Citric Acid | 14.0 |
| Tartaric Acid | 28.1 |
| Sodium Bicarbonate | 47.9 |
| Rotunculus | 4.0 |
| Symphytum | 2.0 |
| Calendula | 2.0 |
| Cupressus oil | 2.0 |

EXAMPLE 9

In this example, the dry herbal extracts are prepared from Echinacea and *Inula helenium*. The essential oils are prepared from Thymus Serpilium, *Saturea montana* and *Origanum vulgare*.

| Ingredients | % w/w |
| --- | --- |
| Citric Acid | 14.0 |
| Tartaric Acid | 28.1 |
| Sodium Bicarbonate | 47.9 |
| Echinacea | 2.5 |
| *Inula helenium* | 2.5 |
| *Thymus Serpilium* | 1.5 |
| *Saturea montana* | 2.0 |
| *Origanum vulgare* | 1.5 |

EXAMPLE 10

In this example, extracts prepared from Phytolacca, Calendula and Hamamelis plants are the dry herbal extracts. Thyme oil, Lavender oil and Tea Tree oil are the essential oils.

| Ingredients | % w/w |
| --- | --- |
| Citric Acid | 12.0 |
| Tartaric Acid | 24.0 |
| Sodium Bicarbonate | 54.0 |
| Phytolacca | 2.0 |
| Calendula | 1.0 |
| Hamamelis | 1.0 |
| Thyme oil | 2.0 |
| Lavender oil | 2.0 |
| Tea Tree oil | 2.0 |

EXAMPLE 11

In this example, extracts prepared from Phytolacca, Calendula, Hamamelis and Arnica plants, as well as Propolis extract, are the dry herbal extracts. Thyme oil, Lavendula oil and Geranium oil are the essential oils.

| Ingredients | % w/w |
| --- | --- |
| Citric Acid | 12.0 |
| Tartaric Acid | 24.0 |
| Sodium Bicarbonate | 39.0 |
| Phytolacca | 4.0 |
| Calendula | 3.0 |
| Hamamelis | 3.0 |
| Arnica | 4.5 |
| Propolis | 4.5 |

| Ingredients | % w/w |
|---|---|
| Thyme oil | 2.0 |
| Lavendula oil | 2.0 |
| Geranium oil | 2.0 |

EXAMPLE 12

In addition to these eleven previous Examples, two formulations of effervescent salts according to the present invention were both prepared and tested according to a protocol described in detail below. Briefly, the effervescent salts were prepared and were then placed in water to dissolve. Both formulations described below dissolved rapidly and completely. Thus, effervescent salts formulated according to the present invention are effective as vehicles for herbal preparations.

The particular advantage of these two formulations is that they contain a soap (sodium lauryl sulfate) so that they produce foam when contacted with water. Like the previous formulations, these two formulations are also effervescent. Thus, effervescent salts prepared according to these two formulations can act as bath foam with an effervescent effect when added to bathing water, for example.

In this Example, the formulation tested was for vehicle only with dry powdered ingredients as listed below.

| Ingredients | % w/w |
|---|---|
| Citric Acid | 12.0 |
| Tartaric Acid | 24.0 |
| Sodium Bicarbonate | 39.0 |
| Sodium Lauryl sulfate | 10.0 |
| Lactose | 15.0 |

The dried powdered ingredients listed above were mixed. Next, a moistening agent was added to the mixture. The moistening agent was 90% ethanol and 10% water. As an example of a suitable ratio between the moistening agent and the dry ingredients, if the powdered ingredients weighed 250 grams total, then 23 ml of moistening agent was used, although of course other proportions would be possible. After the moistening agent was added, then the moistened powder mixture was pressed through a screen of mesh size 600. Finally, the resultant granules were dried in an oven at about 55–58° C. for three hours, to form the effervescent salt vehicle of the present invention.

The granules of the effervescent salt vehicle were placed in water, where they dissolved completely and rapidly. Furthermore, a large amount of foam was formed, indicating the efficient release of large amounts of carbon dioxide. Thus, the effervescent salt vehicle of this Example was an effective formulation.

EXAMPLE 13

A second formulation was tested, as describe in this Example. Again, the formulation tested was for vehicle only with dry powdered ingredients as listed below.

| Ingredients | % w/w |
|---|---|
| Citric Acid | 12.0 |
| Tartaric Acid | 24.0 |
| Sodium Bicarbonate | 39.0 |
| Sodium Lauryl sulfate | 20.0 |
| Lactose | 5.0 |

The formulation was prepared as for Example 12, including the same relative amount of the same moistening agent. Again, the resultant granules were placed in water, where they dissolved completely, although less rapidly than those of the formulation of Example 12. Although foam was formed as a result, the amount of foam was less than that formed previously, indicating the release of less carbon dioxide. However, these tests indicate that the effervescent salt vehicle of this Example was still an effective vehicle formulation.

It will be appreciated that the above descriptions are intended only to serve as examples, and that many other embodiments are possible within the spirit and the scope of the present invention.

What is claimed is:

1. A formulation of an effervescent granule, comprising:
    (a) a pharmaceutically effective amount of a herbal medication;
    (b) an acid;
    (c) a base capable of releasing carbon dioxide upon reaction with said acid when contacted with water; and
    (d) a soap,
   wherein said soap is sodium lauryl sulfate.

2. The effervescent granule of claim 1, wherein said acid is selected from the group consisting of tartaric acid and citric acid.

3. The effervescent granule of claim 1, wherein said acid is a mixture of tartaric acid and citric acid.

4. The effervescent granule of claim 3, wherein said tartaric acid and said citric acid are present in a ratio of about 2:1 by weight.

5. The effervescent granule of claim 1, wherein said base is selected from the group consisting of sodium bicarbonate, sodium carbonate and potassium bicarbonate.

6. The effervescent granule of claim 5, wherein said base is sodium bicarbonate.

7. The effervescent granule of claim 6, wherein said acid is a mixture of citric acid and tartaric acid, and said sodium bicarbonate, said citric acid and said tartaric acid are present in a ratio of about 3.44:1:2 by weight.

8. A method of releasing and evenly dispersing a medication in water, comprising the steps of:
    (a) providing a formulation of an effervescent granule, said granule containing;
        (i) a pharmaceutically effective amount of a herbal medication;
        (ii) an acid;
        (iii) a base capable of releasing carbon dioxide upon reaction with said acid when contacted with water; and
        (iv) a soap,
    wherein said soap is sodium lauryl sulfate and
    (b) placing said granule in water, such that the medication is released upon reaction of said acid and said base.

9. An effervescent granule comprising:
    (a) a medication consisting essentially of a herbal medication;

(b) an acid; and (c) a base capable of releasing carbon dioxide upon reaction with said acid when contacted with water.

10. An effervescent granule consisting essentially of:

(a) a pharmaceutically effective amount of a herbal medication, as medicinal agent;

(b) an acid; and (c) a base capable of releasing carbon dioxide upon reaction with said acid when contacted with water.

11. A method of releasing and evenly dispersing a medication in water, comprising the steps of:

(a) providing an effervescent granule, said granule containing;

(i) a medication consisting essentially of a herbal medication;

(ii) an acid; and (iii) a base capable of releasing carbon dioxide upon reaction with said acid when contacted with water; and (b) placing said granule in water, such that the medication is released upon reaction of said acid and said base.

12. The effervescent granule of claim 9, wherein said acid is selected from the group consisting of tartaric acid and citric acid.

13. The effervescent granule of claim 9, wherein said acid is a mixture of tartaric acid and citric acid.

14. The effervescent granule of claim 13, wherein said tartaric acid and said citric acid are present in a ratio of about 2:1 by weight.

15. The effervescent granule of claim 9, wherein said base is selected from the group consisting of sodium bicarbonate, sodium carbonate and potassium bicarbonate.

16. The effervescent granule of claim 15, wherein said base is sodium bicarbonate.

17. The effervescent granule of claim 16, wherein said acid is a mixture of citric acid and tartaric acid, and said sodium carbonate, said citric acid and said tartaric acid are present in a ratio of about 3.44:1:2 by weight.

* * * * *